United States Patent [19]
Levine et al.

[11] Patent Number: 5,843,684
[45] Date of Patent: Dec. 1, 1998

[54] METHOD FOR DETECTING PRE-CANCEROUS OR CANCEROUS CELLS USING P90 ANTIBODIES OR PROBES

[75] Inventors: Arnold J. Levine, Princeton, N.J.;
 Cathy A. Finlay, Chapel Hill, N.C.;
 Carlos Cordon-Cardo, New York, N.Y.

[73] Assignee: The Trustees of Princeton University, Princeton, N.J.

[21] Appl. No.: 362,590

[22] PCT Filed: Jun. 28, 1993

[86] PCT No.: PCT/US93/06163

§ 371 Date: Mar. 31, 1995

§ 102(e) Date: Mar. 31, 1995

[87] PCT Pub. No.: WO94/00603

PCT Pub. Date: Jan. 6, 1994

Related U.S. Application Data

[63] Continuation-in-part of Ser. No. 18,649, Feb. 17, 1993, abandoned, which is a continuation-in-part of Ser. No. 904,766, Jun. 26, 1992, abandoned, which is a continuation-in-part of Ser. No. 730,185, Jul. 12, 1991, abandoned, which is a continuation-in-part of Ser. No. 543,963, Jun. 27, 1990, abandoned.

[51] Int. Cl.$^6$ ........................ G01N 33/574; C07K 16/30
[52] U.S. Cl. ........................ 435/7.23; 435/6; 435/326; 436/64; 436/813; 530/388.8; 530/388.85; 530/387.7
[58] Field of Search ................ 435/7.23, 6, 326; 436/64, 813; 530/388.8, 388.85, 387.7

[56] References Cited

U.S. PATENT DOCUMENTS 4,762,706  8/1988  McCormick et al. ................ 435/7.23

OTHER PUBLICATIONS

Cahilly–Snyder, L. et al., *Somatic Cell and Molecular Genetics*, vol. 13, No. 3, pp. 235–244, 1987.
Fakharzadeh, et al., *EMBO Journal*, vol. 10, No. 6, pp. 1565–1569, 1991.
Hinds, et al., *Cell Growth & Differentiation*, vol. 1, pp. 571–580, Dec. 1990.
Werness et al., Science, vol. 248, pp. 76–79, 6 Apr. 1990.

*Primary Examiner*—Toni R. Scheiner
*Attorney, Agent, or Firm*—Irving N. Feit; Thomas C. Gallagher; Laura S. Weiss

[57] ABSTRACT

The invention provides a method of diagnosing cancer by determining the expression level or gene amplification of p53 and dm2, whereby an elevated level of either p53 or dm2 or both p53 and dm2 indicates a cancer diagnosis. Furthermore, the invention provides a method of predicting the progress of cancer by determining the expression level or gene amplification of p53 and dm2, whereby an elevated level of either p53 or dm2 or both p53 and dm2 indicated a poor prognosis.

34 Claims, 4 Drawing Sheets

METHOD FOR DETECTING PRE-CANCEROUS OR CANCEROUS CELLS USING P90 ANTIBODIES OR PROBES

This application is a continuation-in-part of PCT Application No. PCT/US93/06163, filed Jun. 28, 1993, which is a continuation-in-part of U.S. Ser. No. 08/018,649, filed Feb. 17, 1993, now abandoned, which is a continuation-in-part of U.S. Ser. No. 07/904,766, filed Jun. 26, 1992, now abandoned, which in turn is a continuation-in-part of U.S. Ser. No. 07/730,185, filed Jul. 12, 1991, now abandoned, which in turn is a continuation-in-part of U.S. Ser. No. 07/543,963 filed Jun. 27, 1990, now abandoned, all of which are incorporated herein by reference.

BACKGROUND OF THE INVENTION

Mutations of proto-oncogenes in somatic cells are increasingly being recognized as significant in the induction of human cancers. Some examples of oncogenes formed by such mutations include: neu, fes, fos, myc, myb, fms, Ha-ras, and Ki-ras. The mutations that convert proto-oncogenes to oncogenes are often point mutations. Much needs to be learned in order to understand how oncogenes and their expression products function to transform normal cells to cancer cells.

Oncogenes are generally believed to act in a dominant fashion. This is generally considered to mean that the conversion of a proto-oncogene to an oncogene results in the acquisition of a new function, i.e., enhancing transformation.

A different type of mutation associated with cancer occurs when a tumor suppressor gene is altered in a way that causes the product of the gene to lose its tumor suppressor function. An example of such a tumor suppressor gene is the retinoblastoma susceptibility gene, Rb. Tumor suppressor genes are sometimes called recessive oncogenes, although, strictly speaking, the products of tumor suppressor genes do not contribute to tumor formation. The phenotype is recessive since, when both alleles are mutated, the absence of a tumor suppressor gene results in an enhancement of tumorigenesis.

A gene product that exhibits some properties of both a dominant and a recessive oncogene is the 53 kd phosphoprotein, p53. Evidence is growing that mutations in the p53 gene is associated with a large number of many types of cancers. For example, Iggo et al., Lancet 335, 675–679 (1990) has expressed the opinion that p53 is the most common proto-oncogene to undergo mutation in lung cancers.

Much of what is known about p53 has been derived from studying the effect of transfecting wild-type and mutant murine p53 in rat embryo fibroblast cells. This work has been reviewed by Levine et al., "The P53 Proto-Oncogene And Its Product," in *Common Mechanisms of Transformation By Small DNA Tumor Viruses*, L. Villarreal, ed., American Society for Microbiology, Chapter 2 (1989); Hinds et al., ibid, Chapter 7; and Levine, BioEssays 12, 60–66 (1990).

The p53 gene appears to be involved in transcriptional control (Fields, S. & Jang, S. K. (1990) *Science* 249, 1046–1049; Raycroft, L., Wu, H. & Lozano, G. (1990) *Science* 249, 1049–1051; and Levine, A. J., Momand, J. & Finlay, C. A. (1991) *Nature* 351, 453–456) and may act as a regulatory check point in the cell cycle, arresting cells in the G-1 phase (Martinez, J., Georgoff, I. & Levine, A. J. (1991) *Genes Dev.* 5, 151–159; Hupp, T. R., Meek, D. W., Midgley, C. A. & Lane, D. P. (1992) *Cell* 71, 875–886; and Yin, Y., Tainsky, M. A., Bischoff, F. Z., Strong, C. C. & Wahl, E. M. (1992) *Cell* 70, 937–948). Genetic alterations of the p53 gene, such as intragenic mutations, homozygous deletions, and structural rearrangements, are frequent events in human cancer (Vogelstein, B. & Kinzler, K. (1992) *Cell* 70, 523–526; Baker, S. J. et al. (1990) *Cancer Res* 50, 7717–7722; Mori, N. et al. (1989) *Cancer Res* 49, 5130–5135; Lee, J. H. et al. (1990) *Cancer Res* 50, 2724–2728; Varley, J. M. et al. (1991) *Oncogene* 6, 413–421; Presti, J. C. et al. (1991) *Cancer Res* 51, 5405; Dalbagni, G., et al. (1993) *Diagnostic Molecular Pathology* 2, 4–13). These altered patterns of p53 either reduce or inhibit the activity of functional homotetramer units (Stenger, J. E., et al. (1992) *Mol Carcinog* 5, 102–106; Sturzbecher, H. W., et al. (1992) *Oncogene* 7, 1513–1523). Mutant p53 proteins have a prolonged half-life and retarded degradation, yielding accumulation of inactive complexes and self-aggregatory molecules in the nuclei of tumor cells (Sturzbecher, H. W. et al. (1987) *Oncogene* 1, 201–211; Halevy, O. et al. (1989) *Mol Cell Biol* 9, 3385–3392), In humans, germ-line mutations of the p53 gene have been characterized in members of families affected with the Li-Fraumeni syndrome, a rare autosomal dominant trait that predisposes these individuals to develop a variety of tumors, including soft tissue sarcomas (Li, F. P. & Fraumeni, J. F. (1969) *Ann Intern Med* 71, 747–752; Malkin, D. et al. (1990) *N. Engl. J. Med.* 250, 1233–1238). More recently, p53 germ-line mutations were also detected in cancer patients with no apparent family history of cancer (Toguchida, J. et al. (1992) *N. Engl. J. Med.* 326, 1301–1308), as well as a subset of patients presenting with a second primary neoplasm (Malkin D., et al. (1992) *New Eng J Med* 326, 1309–1315). In addition, somatic mutations of the p53 gene have been reported to occur in soft tissue sarcomas (Stratton, M. R., et al. (1990) *Oncogene* 5, 1297–1301; Mulligan, L. M., et al. (1990) *Proc Natl Acad Sci USA* 87, 5863–5867; Toguchida, J. et al. (1992) *Cancer Res* 52, 6194–6199; Drobnjak, M. et al. (1993) Submitted; Latres, E., et al. (1993) Submitted).

Another gene that has been identified as having oncogenic potential is the murine double minute-2 (mdm2) gene (Fakharzadeh et al., (1991) *The EMBO Journal* 10(6):1565–1569). The sequences of the murine and human mdm2 genes and proteins are known (Fakharzadeh et al., The EMBO Journal 10(6):1565–1569 (1991); Oliner, J. D. et al. (1992) *Nature* 358:80–83; and Cahilly-Snyder et al., Somatic Cell and Molecular Genetics, 13(3):235–244 (1987)). The sequence is evolutionarily conserved among species including mouse, rat, hamster and human genomes (Cahilly-Snyder et al., Somatic Cell and Molecular Genetics, 13(3):235–244 (1987)).

The mdm2 gene is also referred to in the literature as MDM2, MDM2 and hdm2 (the human homologs) and mdm2 (murine). The mdm2 gene product, which is a 90 kD phosphoprotein, is referred to in the literature as p90, which refers to both murine and human homologs, and MDM2, which is the human homolog. The p90 protein is described in applicants' related publication, Levine et al., International Application No. PCT/US91/04608, filed Jun. 27, 1991. Where dm2 is used throughout this application, it is meant to encompasses the various terms in the literature for the mdm2 gene and protein, including homologs among all species.

There is evidence for MDM2 amplification and MDM2 (gene product) overexpression in both osteo- and soft tissue sarcomas (Oliner, J. D. et al. (1992) *Nature* 358, 80–83; Ladanyi, M. et al. (1993) *Cancer Res* 53, 16–18; Leach, F. S. et al. (1993) *Cancer Res* 53, 2231–2234).

The human homolog of the mdm2 gene, called the hdm2 gene or MDM2 or MDM2, has been cloned and mapped to the long arm of chromosome 12 (12q13–14) (Oliner et al. 1992. Amplification of a gene encoding a p53-associated protein in human sarcomas. Nature 358:80–83). This region contains two genes, SAS and GLI, previously found to be amplified in osteo- and soft tissue sarcomas. The SAS gene codes for a protein of unidentified function. It was isolated from a malignant fibrous histiocytoma (MFH), and was shown to be amplified in MFH and liposarcomas (Turc-Carel, C. et al. (1986) *Cancer Genet Cytogenet* 23, 291–299; Meltzer, P. S. et al. (1991) *Cell Growth Diff* 2, 495–501). The GLI gene codes for a DNA-binding zinc finger protein. Even though it was originally isolated from a glioblastoma, it has also been reported to be amplified in a rhabdomyosarcoma and an osteosarcoma (Kinzler, K. et al. (1984) *Science* 236, 70–73).

Prior to the present invention, it was known that mutated p53 is associated with cancer. Futhermore, it was known prior to the present invention that overexpression of mdm2 is associated with tumors. However, there has been no disclosure prior to the present invention of the relationship between altered p53 and dm2 genes and their altered patterns of expression in cells and how to utilize this relationship to diagnose as well as to determine the clinical relevance or prognoses of cancer patients. An objective of the subject invention is to utilize the relationship between p53 and dm2 overexpressed or amplified genes to diagnose cancer as well as to determine the prognoses of cancer patients.

SUMMARY OF THE INVENTION

The subject invention provides a method of diagnosing cancer by determining the level of p53 and dm2 in a biological sample, whereby an elevated level of either p53 or dm2 or both p53 and dm2 indicates a cancer diagnosis.

A further objective of the invention has been met by providing a method of predicting the progress of cancer by determining the level of p53 and dm2 in a biological sample, whereby an elevated level of either p53 or dm2 or both 53 and dm2 indicates a poor prognosis.

The invention further provides a method of classifying a biological sample into one of three groups, the method comprising determining whether the level of either p53 or dm2 in the sample is abnormally elevated, whereby the first group comprises no abnormal elevation of either the level of p53 or dm2, the second group comprises abnormal elevation of the level of p53 and no abnormal elevation of the level of dm2 or abnormal elevation of the level of dm2 and no abnormal elevation of the level of p53, and the third group comprises abnormal elevation of the level of both p53 and dm2.

The invention further provides a method of detecting in a biological sample cancer cells or cells at risk of becoming cancerous or pre-cancerous, wherein the cells contain at least one normal p53 allele. The method comprises determining whether the level of dm2 in the biological sample is abnormally elevated, whereby an elevated level of dm2 in the biological sample in comparison to normal biological samples indicates cancer cells or cells at risk of becoming cancerous or pre-cancerous.

The invention also provides an isolated p53/dm2 protein complex and antibodies to the dm2 protein.

BRIEF DESCRIPTION OF THE FIGURES

FIG. 4: This photograph illustrates immunostaining patterns using anti-dm2 and anti-p53 antibodies. The control group refers to the top two slides. The top left slide shows a staining pattern of a 3T3-Balb/c cell line, which is dm2−. The top right slide shows a staining pattern of 3T3-DM cell line, which is dm2+. The middle two slides show a staining pattern of human tumor tissue sections taken from the same patient. The middle left slide shows a p53− staining pattern, and the middle right slide shows a dm2+ staining pattern (corresponding to the Group B subset p53−/dm2+ subset described below). The bottom two slides show a staining pattern of human tumor tissue sections taken from different patient. The bottom left slide shows a p53+ staining pattern, and the bottom right slide shows a dm2+ staining pattern (corresponding to Group C described below).

DETAILED DESCRIPTION OF THE INVENTION

Definitions:

p53:

For the purposes of the present specification, the term "wild-type" p53 means the nucleotide or amino acid sequence reported by Matlashewski et al., EMBO J. 13, 3257–3262 (1984); Zakut-Houri et al., EMBO J. 4, 1251–1255 (1985); and Lamb and Crawford, Mol. Cell. Biol. 5, 1379–1385 (1986). The sequences are available from GenBank. Wild-type p53 includes a proline/arginine polymorphism at amino acid 72 and the corresponding nucleotide polymorphism.

Mutations of wild-type p53 genes and proteins indicate pre-cancer and cancer states. A pre-cancer cell is a cell that typically has one normal p53 allele and one mutated p53 allele. For example, the mutation may be a point mutation. In a cancer cell, both p53 alleles are usually mutated. For example, one mutation may be a point mutation, and the other mutation may be a deletion of all or a significant part of the p53 gene.

dm2:

The dm2 of this invention refers to a family of proteins that includes a phosphoprotein of 90 kD (p90), its fragments or products, including proteins p85 (85 kD), p76 (76 kD), p74 (74 kD) and p58-57 (58 kD and 57 kD) (p57 is the murine equivalent to the rat p58), and homologs or analogs thereof. The p53 protein co-immunoprecipitates with the dm2 protein. The dm2 protein includes the known, sequenced murine double minute 2 (mdm2) 90 kD phosphoprotein. Furthermore, the term "dm2" refers to genes encoding for the family of dm2 proteins described above. The sequence of the mdm2 gene and protein is disclosed by Fakharzadeh et al., The EMBO Journal 10(6):1565–1569 (1991); and Cahilly-Snyder et al., Somatic Cell and Molecular Genetics, 13(3):235–244 (1987)). Sequences homologous to the p90 dm2 are present in the genomes of several species including human ("hdm2") . The human gene has been sequenced and has a molecular weight of approximately 90 kD (Oliner, J. D. et al. (1992) *Nature* 358:80–83), as well as rat, mouse and hamster. In a preferred embodiment, the dm2 gene and protein are human.

dm2 proteins of approximately 90 kD clearly, and p58 most likely, binds to p53. 3T3DM cells derived from Balb/c 3T3 overproduce the five mdm2 protein species in response to the amplified mdm2 gene copy.

Elevated Levels of dm2 and/or p53 (dm2+ and/or p53+):

For the purposes of this specification, elevated levels of dm2 and/or p53 in a cell may indicate dm2 or p53 gene amplification, or of dm2 or p53 protein product overexpression or accumulation in a biological sample, such as a cell. Elevated levels of dm2 or p53 protein are a measure of total dm2 or p53 protein in a biological sample, preferably a cell, whether free protein or in a complex. In some cases, the dm2 protein elevated levels in the absence of dm2 amplification indicates the formation of heterodimers/heterotetramers between dm2 and mutated p53 products. Mutant p53 proteins have a prolonged half-life and retarded degradation, and therefore accumulate in the cell nuclei. p53 missense mutations represent the majority, at least about 85%, of the p53 mutations detectable by immunochemistry. However, in some cases, wild-type p53 genes and proteins are detected at elevated levels in tumor issue.

An elevated level of dm2 and/or p53 in a biological sample in comparison to normal biological samples indicates a cancer cell or cell at risk of becoming cancerous or pre-cancerous. A biological sample may include but is not limited to, tissue extracts, cell samples or biological fluids such as lymph, blood or urine.

The subject invention provides a method of classifying a biological sample into one of three groups, the method comprising determining whether the level of either p53 or dm2, or both p53 and dm2, in the sample is abnormally elevated. The first group, Group A, comprises no abnormal elevation of either the level of p53 or dm2 (p53–/dm2–); the second group, Group B, comprises abnormal elevation of the level of dm2 and no abnormal elevation of the level of p53 (p53–/dm2+), or abnormal elevation of the level of p53 and no abnormal elevation of the level of dm2 (p53+/dm2–); and the third group, Group C, comprises abnormal elevation of the level of both p53 and dm2 (p53+/dm2+).

The invention demonstrates that classifying altered patterns of dm2 and p53 expression is clinically significant for the diagnosis and prediction of the clinical outcome of patients with various types of cancer. Such cancers include sarcomas, carcinomas and leukemias or lymphomas. Particularly, such cancers include sarcomas, such as soft tissue sarcomas and osteogenic sarcomas. In another embodiment, the cancers include bladder cancers. Other embodiments include, but are not limited to, colorectal, lung, ovarian, cervical, adrenal cortex, bone, breast, brain, chronic myelocytic leukemia, and chronic myelogenous leukemia. Therefore, the invention provides a method of assessing a subject's prognosis by obtaining a biological sample from pre-cancer tissue or a tumor of the subject, and determining to which of the three groups, A, B, or C, the biological sample belongs. Of the three categories, the third group indicates the worst prognosis and the first group indicates the best prognosis.

Group C (D53+/dm2+):

The invention provides a method for detecting a cancer cell or cell at risk of becoming cancerous or pre-cancerous, wherein the cell contains at least one mutant p53 allele, by determining whether elevated levels of dm2 are present.

Figure 3:
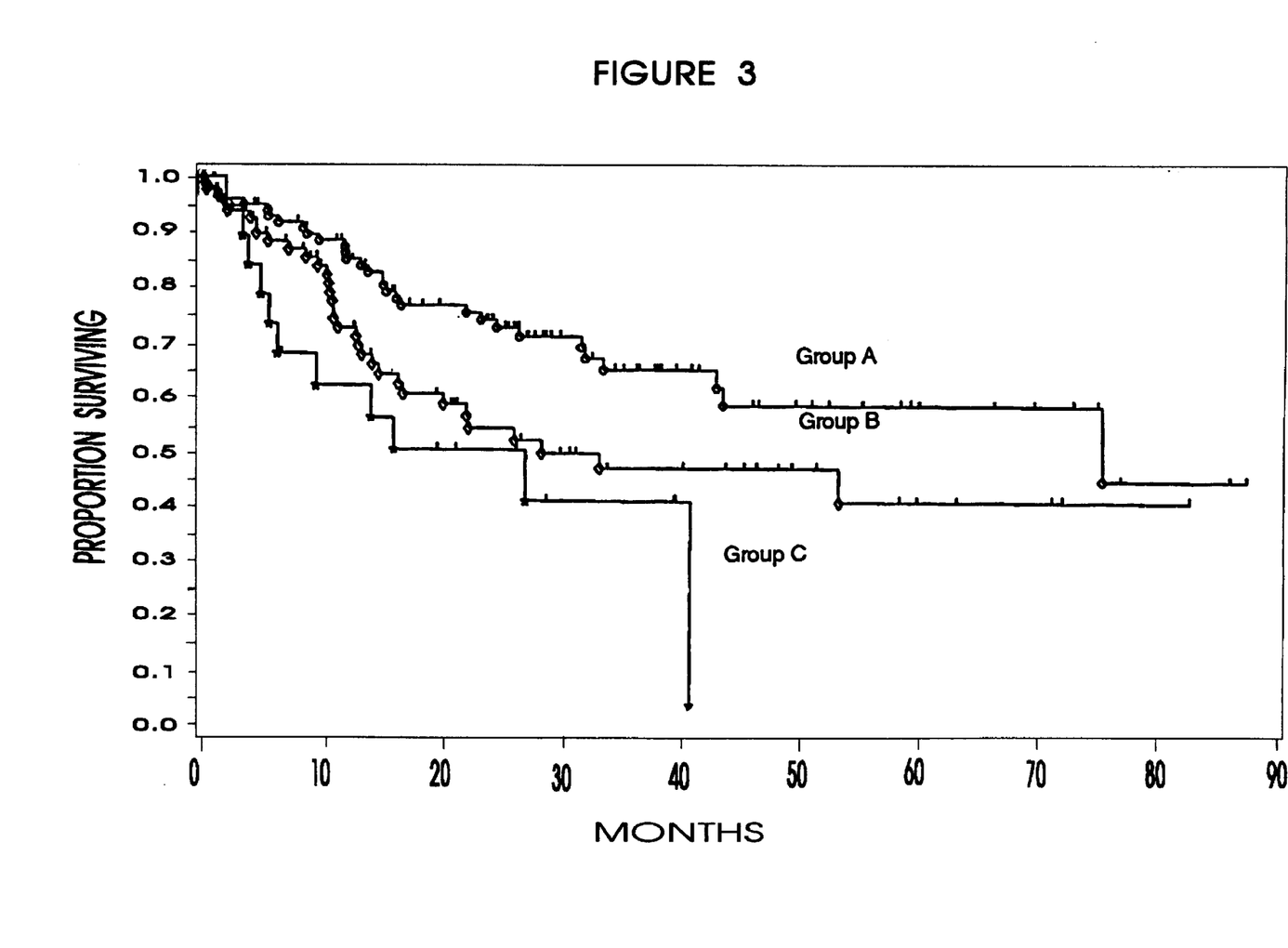
FIG. 3: This graph shows p53/mdm2 elevated levels and survival in the group of 211 patients (see FIG. 2) with soft tissue sarcomas. The phenotypic categories shown in the graph are as follows: Group A: dm2−/p53− (neither dm2 nor p53 had elevated levels); Group B: dm2+/p53− and dm2−/p53+; and Group C: dm2+/p53+ (elevated levels of both dm2 and p53).
Figure 4:
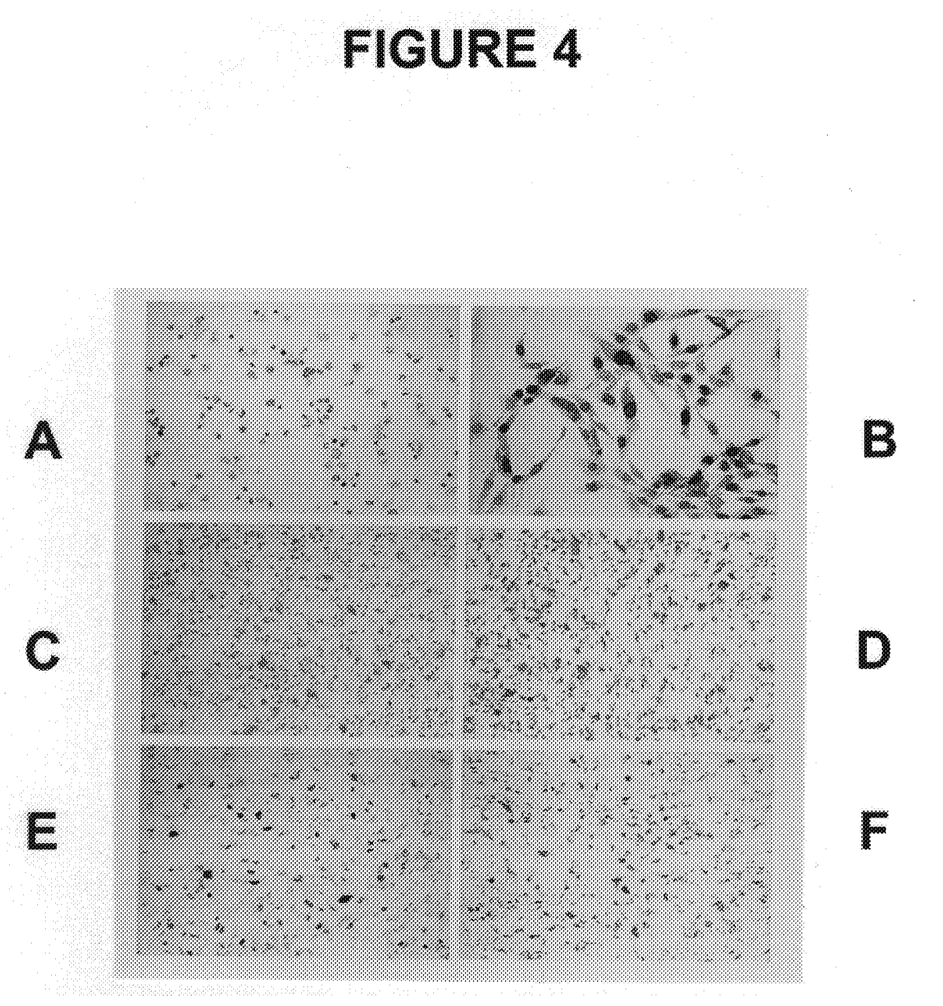

The invention unexpectedly demonstrates that elevated levels of dm2 protein act synergistically with elevated levels of p53 protein, including mutant as well as overexpressed wild-type forms of p53 protein, which may be detected as elevated levels of p53, i.e., the p53+/dm2+group (see FIG. 4), resulting in clinicopathological variables of poor prognosis, including survival and tumor progression. Of the three groups, Group C indicates the worst prognosis. Example 2 and FIG. 3 show that the immunological detection of abnormally elevated levels of dm2 and p53 in the same tumor sections occurred in a group with very poor survival when compared to Groups A (no p53 or dm2 elevated levels) and B (elevated levels of only one of these proteins).

This is unexpected because, as discovered by the inventors, dm2 protein inactivates p53 transcriptional activity, and therefore one might not have expected elevated levels of dm2 protein in a cell with elevated levels of p53 protein.

Group B (p53–/dm2+and p53+/dm2–)

Group B contains two subsets, normal levels of p53 with elevated levels of dm2 (p53–/dm2+) and elevated levels of p53 with normal levels of dm2 (p53+/dm2–) . Of the three groups, Group B indicates a poorer prognosis than Group A, but better prognosis than Group C.

subset p53+/dm2– of Group B:

The detection of elevated levels of p53, such as mutated or overexpressed wild-type p53 genes and proteins, i.e. the p53+/dm2– group, indicate pre-cancer and cancer states. Mutant forms of p53 can inactivate the wild-type p53 function, and cells containing mutant p53 genes and proteins have an enhanced tumorigenic potential. Furthermore, elevated levels of wild-type p53 protein may contribute to poor prognosis. DNA damage in cells or binding to viral oncogene products stabilize wild-type p53 protein and increase its concentration.

subset p53–/dm2+of Group B:

The invention unexpectedly demonstrates that elevated levels of dm2 confer a similar property on cells, such as such as BALB/c 3T3 cells (3T3 DM cells) or pre-cancer or cancer cells, as does elevated levels of p53. In both cases, the cells that express high levels of dm2 or p53 protein gain an enhanced tumorigenic potential in animals.

The invention provides that, with regard to the p53–/dm2+ group, despite the presence of normal levels of wild-type p53 allele or alleles in a cell, elevated levels of dm2 enhance the tumorigenic potential of the cell.

The invention provides a method of detecting a cancer cell or cell at risk of becoming cancerous or pre-cancerous wherein the cell contains two normal p53 alleles, i.e. wild-type p53, or normal levels of p53, comprising determining whether the level of dm2 in the biological sample is abnormally elevated, meaning elevated in comparison with the level of dm2 in normal biological samples. (see FIG. 4).

Group A (p53–/dm2–)

Group A comprises normal levels of both p53 and dm2. Precancer and cancer cells in this group are most likely due to factors other than elevated levels of p53 and/or dm2. Of the three groups, Group A indicates the best prognosis.

Detection of Elevated Levels OF DM2 OR P53:

Amplification:

Amplification of the dm2 or p53 gene may be detected using methods well known in the art, such as nucleic acid probe technology. High copy numbers of DNA may, for example, be detected using Southern blotting, and increased amounts of RNA may be detected using Northern blotting (see George, D. L. and Powers, V. E., Cell 24:117–123 (1981); George, D. L. et al. EMBO J., 4:1199–1203 (1985); and Singh, L. and Jones, K. W. Nucleic Acids Res., 12:5627–5638 (1984).

Overexpression:

Levels of dm2 and p53 protein in the biological sample are detected by methods well known in the art, such as by using anti-dm2 and anti-p53 antibodies and immunohistochemical staining. A positive nuclear staining when using immunohistochemistry indicate elevated levels of p53 or dm2 or p53/dm2 complexes. Overexpressed p53 proteins are associated with p53 gene mutations. In one embodiment of the invention, dm2 and p53 nuclear overexpression in tumors is classified into one of three groups by estimating the percentage of tumor cell nuclei staining: (a) negative (<20%), (b) heterogeneous (20–70%), (c) homogeneous (>70%).

In another embodiment of the invention, the elevated level of dm2 is detected by a method indicating that a pre-cancer or cancer state is 2–100 times that of normal biological samples, such as cells. In a preferred embodiment, the elevated level is a level 5–50 times that of normal biological samples, such as cells.

Polyclonal and monoclonal antibodies may be prepared by methods known in the art. Antibodies of this invention include recombinant polyclonal or monoclonal Fab fragments prepared in accordance with the method of Huse et al., Science 246:1275–1281 (1989). See Campbell, "Monoclonal Antibody Technology, The Production and Characterization of Rodent and Human Hybridomas" in Burdon et al., Eds, Laboratory Techniques in Biochemistry and Molecular Biology, Volume 13, Elsevier Science Publishers, Amsterdam (1985).

Methods for preparing polyclonal and monoclonal antibodies that exhibit specificity toward single amino acid differences between oncogenes are described by McCormick et al. in U.S. Pat. No. 4,798,787.

Briefly, polyclonal antibodies may be produced by injecting a host mammal, such as a rabbit, mouse, rat, or goat, with the p53 protein or a fragment thereof capable of producing antibodies that distinguish between mutant p53 and wild-type p53. The peptide or peptide fragment injected may contain the wild-type sequence or the mutant sequence. Sera from the mammal are extracted and screened to obtain polyclonal antibodies that are specific to the peptide or peptide fragment. The same method may be applied to dm2 proteins.

In order to produce monoclonal antibodies, a host mammal is inoculated with a peptide or peptide fragment as described above, and then boosted. Spleens are collected from inoculated mammals a few days after the final boost. Cell suspensions from the spleens are fused with a tumor cell in accordance with the general method described by Kohler and Milstein in Nature 256, 495–497 (1975). In order to be useful, a peptide fragment must contain sufficient amino acid residues to define the epitope of the p53 or dm2 molecule being detected.

If the fragment is too short to be immunogenic, it may be conjugated to a carrier molecule. Some suitable carrier molecules include keyhole limpet hemocyanin and bovine serum albumen. Conjugation may be carried out by methods known in the art. One such method is to combine a cysteine residue of the fragment with a cysteine residue on the carrier molecule.

The peptide fragments may be synthesized by methods known in the art. Some suitable methods are described by Stuart and Young in "Solid Phase Peptide Synthesis," Second Edition, Pierce Chemical Company (1984).

Suitable antibodies for the co-immunoprecipitation of p53 and dm2 include PAb421 and Ab2. PAb421 recognizes the carboxy-terminus of p53 from various species, including human, mouse and rat p53, and is described by Harlow et al. in the Journal of Virology 39, 861–869 (1981). Ab2 is specific for the amino-terminus of human p53, and is available from Oncogene Science, Inc. of Manhassett, N.Y. The dm2 protein does not immunoprecipitate when REF cells that do not express p53 are treated in the same way with the same antibodies.

The immunoprecipitates are recovered by centrifugation. Following centrifugation or elution from the column, dm2 may be separated from the p53/dm2 complex by means of SDS PAGE.

The single band at 90kD is cut and sequenced. This invention also provides an isolated dm2/p53 complex, obtained by the coimmunoprecipitating of dm2 with p53 from a variety of transformed cells.

Another method for purifying dm2 is that generally described by Aebersold et al., Proc. Natl. Acad. Sci. USA 84, 6970–6974 (1987).

This invention provides hybridomas expressing monoclonal antibodies against the dm2 (p90) gene product. Certain of these hybridomas are deposited at the American Type Culture Collection (ATCC): 3G5 ATCC Accession No. HB 11182); 4B11 (ATCC Accession No. HB 11183); 2A10 (ATCC Accession No. HB 11184); 2A9 (ATCC Accession No. 11185); and 4B2 (ATCC Accession No. HB 11186). Hybridomas 3G5, 4B11, 2A10, 2A9 and 4B2, were deposited pursuant to, and in satisfaction of, the requirements of the Budapest Treaty on the International Recognition of the Deposit of Microorganisms for the Purposes of Patent Procedure with the American Type Culture Collection (ATCC), 12301 Parklawn Drive, Rockville, Md. 20852 under ATCC Accession Nos.

HB 11182, HB 11183, HB 11184, HB 11185 and HB 11186, respectively on Nov. 10, 1992, respectively.

Assays for Determining and Modifying the Level of Dm2 in Cells

The level of dm2 and/or p53 in cells is determined by assays known in the art capable of recognizing amplified or overexpressed dm2 and/or p53 genes or proteins.

A variety of assays are available for detecting proteins with labeled antibodies. In a one-step assay, the target molecule, if it is present, is immobilized and incubated with a labeled antibody. The labeled antibody binds to the immobilized target molecule. After washing to remove unbound molecules, the sample is assayed for the presence of the label.

In a two-step assay, immobilized target molecule is incubated with an unlabeled antibody. The target molecule-unlabeled antibody complex, if present, is then bound to a second, labeled antibody that is specific for the unlabeled antibody. The sample is washed and assayed for the presence of the label, as described above.

Labeled anti-dm2 antibodies may be used to detect dm2 using imaging methods. One method for imaging comprises contacting the tumor cell to be imaged with an anti-dm2 antibody labeled with a detectable marker. The method is performed under conditions such that the labeled antibody binds to the dm2. The antibody bound to the dm2 is detected, thereby imaging and detecting the dm2.

The choice of marker used to label the antibodies will vary depending upon the application. However, the choice of marker is readily determinable to one skilled in the art.

These labeled antibodies may be used in immunoassays as well as in histological applications to detect the presence of tumors. The labeled antibodies may be polyclonal or monoclonal. In a preferred embodiment, the antibodies are monoclonal, and are the antibodies deposited with the ATCC listed above.

In preferred embodiments of the invention, the label may be a radioactive atom, an enzyme, or a chromophoric moiety. Some examples of radioactive atoms include $P^{32}$, $I125$, $H^3$, and $C^{14}$. Some examples of enzymes include horseradish peroxidase, alkaline phosphatase, beta-galactosidase, and glucose-6-phosphate dehydrogenase. Some examples of chromophoric moieties include fluorescein and rhodamine. The antibodies may be conjugated to these labels by methods known in the art. For example, enzymes and chromophoric molecules may be conjugated to the antibodies by means of coupling agents, such as dialdehydes, carbodiimides, dimaleimides, and the like. Alternatively, conjugation may occur through a ligand-receptor pair. Some suitable ligand-receptor pairs include, for example, biotin-avidin or -streptavidin, and antibody-antigen.

Antibodies against the dm2 protein may be used to detect elevated levels of the dm2 protein in cells or tissue. In one embodiment, antibodies that are directed at epitopes of dm2 may be used in situ using immunohistopathology techniques. These methods have diagnostic use where there is a high risk of tissue becoming cancerous, such as in polyps or atypical breast tissue, or in tumor cells where there is a greater risk of metastasis or recurrence.

Figure 1:
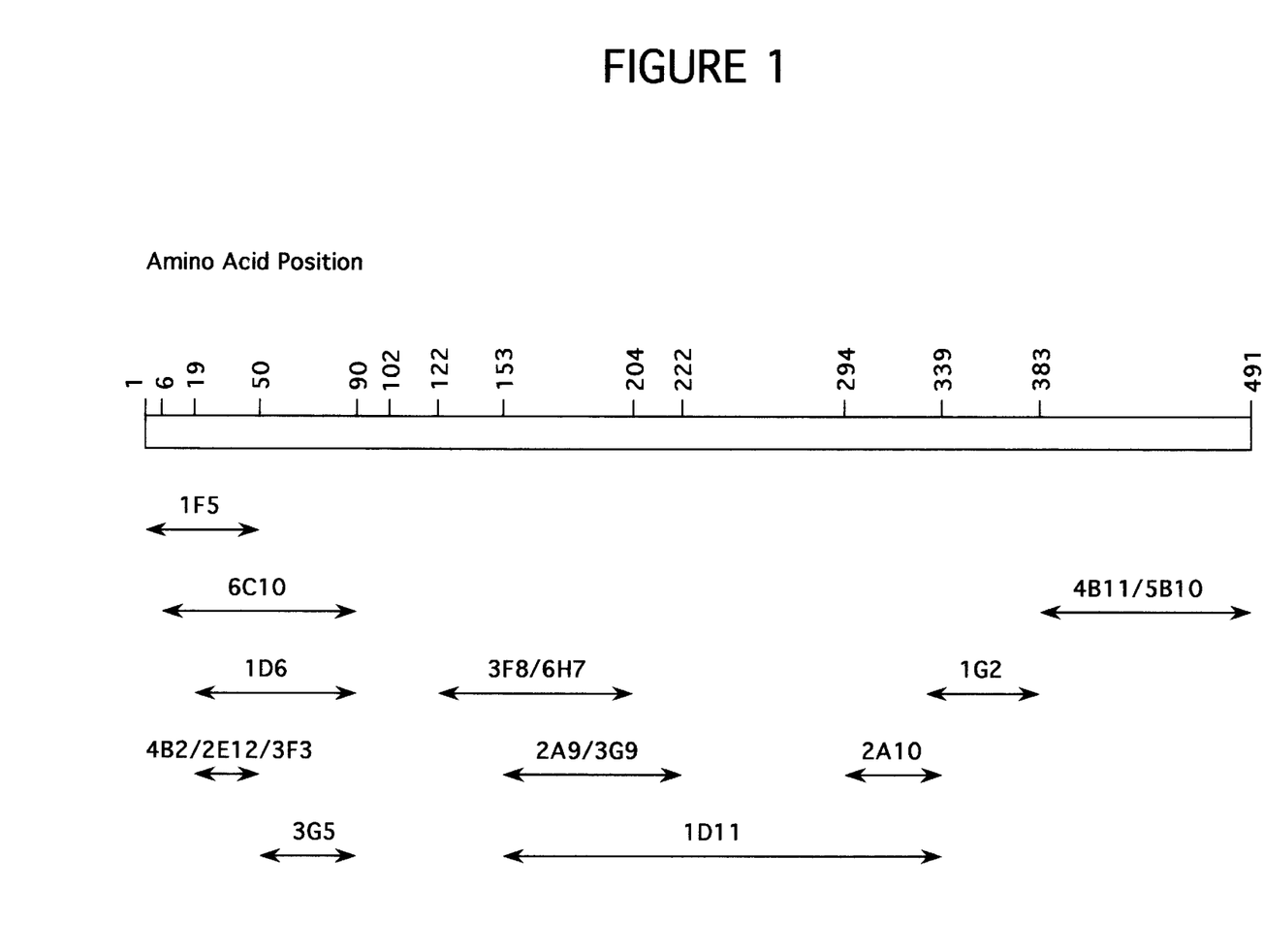
FIG. 1: This figure indicates epitopes of the p90 protein that react with the anti-p90 monoclonal antibodies of the invention. The anti-p90 monoclonal antibodies produced by hybridomas 1F5, 6C10, 1D6, 4B2, 2E12, 3F3, 3G5, 3F8, 6H7, 2A9, 3G9, 1D11, 2A10, 1G2, 4B11 and 5B10 are indicated beneath the p90 amino acid epitope map at locations of the map indicating the epitopes with which such antibodies react.
Figure 2:
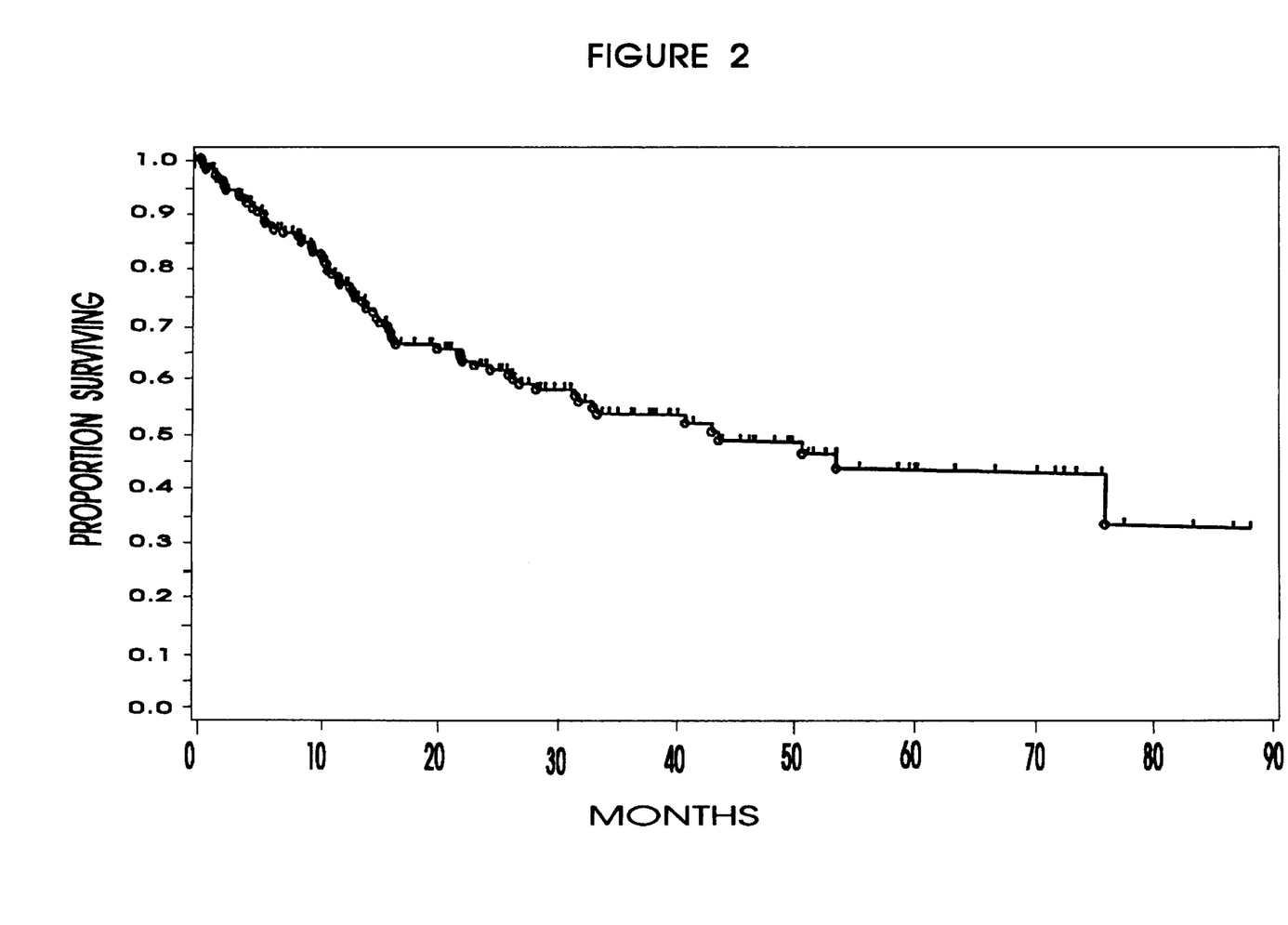
FIG. 2: This graph shows the overall survival of 211 patients with soft tissue sarcomas over a period of 90 months.

The hybridomas 1F5, 6C10, 1D6, 4B2, 2E12, 3F3, 3G5, 3F8, 6H7, 2A9, 3G9, 1D11, 2A10, 1G2, 4B11 and 5B10, some of which were deposited with the ATCC (see above), produce monoclonal antibodies against dm2 protein epitopes (see FIG. 1). The monoclonal antibodies react with both murine and human protein epitopes, as well as with other species, due to the homologous dm2 sequences conserved between the species.

In another embodiment, cancer cells may release dm2 and herefore increase the amount of dm2 in the blood or lymph of a subject. Therefore, assays such as immunoassays may be used to detect normal levels or levels of dm2 above normal in cells or bodily fluids.

Screening for Therapeutics to Block dm2 Binding to Wild-Type p53:

Assays may be used to screen for therapeutics to inhibit dm2 binding to wild-type p53. The subject invention discloses methods for selecting a therapeutic which forms a complex with dm2 with sufficient affinity to prevent the deleterious binding of dm2 to wild-type p53. The methods include various assays, including competitive assays where the dm2 is immobilized to a support, and is contacted with both wild-type p53 and a labeled therapeutic either simultaneously or in either consecutive order, and determining whether the therapeutic effectively competes with the wild-type p53 in a manner sufficient to prevent binding of dm2 to wild-type p53. In another embodiment, the wild-type p53 is labeled and the therapeutic is unlabeled. In a further embodiment, the p53 is immobilized to a support, and is contacted with both labeled dm2 and a therapeutic (or unlabeled dm2 and a labeled therapeutic), and determining whether the amount of dm2 bound to the p53 is reduced in comparison to the assay without the therapeutic added. The dm2 may be labeled with the anti-dm2 antibodies of the subject invention.

In one embodiment, the method comprises:

a) contacting a solid support with a predetermined amount of dm2 under conditions permitting dm2 to attach to the surface of the support, such as by using an anti-dm2 antibody to tether the dm2 to the solid support; b) removing any dm2 which is not bound to the support; c) contacting the solid support to which the dm2 is bound with wild-type p53 under conditions such that the wild-type p53 binds to the bound dm2 and forms a complex therewith; d) removing any unbound p53; e) contacting the dm2/p53 complex so formed with a predetermined amount of the sample labeled with a detectable marker under conditions such that the labeled potential therapeutic present in the sample competes with the wild-type p53 for binding to the bound dm2; f) quantitatively determining the concentration of labeled potential therapeutic not bound to the solid support; and g) thereby quantitatively determining the concentration of potential therapeutic in the sample that specifically binds to dm2 to block dm2 binding to wild-type p53.

The choice of solid support may be readily determined by one skilled in the art. In one preferred method, the solid support is a bead formed of an inert polymer, in another the solid support is a microwell. The markers used in the above-described method are a matter of choice to one skilled in the art. It is preferred that the detectable marker is an enzyme, a paramagnetic ion, biotin, a fluorophore, a chromophore, a heavy metal, or a radioisotope. More preferably, the marker is an enzyme, and most preferably, the enzyme is horseradish peroxidase or alkaline phosphatase.

A further embodiment of this method is wherein the potential therapeutic is labeled with an enzyme and step (f) comp-rises removing the labeled potential therapeutic which was not bound to the solid support and contacting it with specific substrate to the enzyme under conditions such that the enzyme reacts with the substrate to form a detectable product.

The subject invention also provides a method of treating cancer in mammals including mice, rats, hamsters and humans, which comprises blocking the deleterious binding of dm2 to wild-type p53. One embodiment of this method comprises blocking the binding of dm2 to wild-type p53 by contacting the dm2 with a sufficient amount of anti-dm2 antibody. Another embodiment of this method comprises blocking the binding of dm2 to wild-type p53 by contacting the dm2 with an excess of an anti-idiotypic p53 antibody. In another embodiment, dm2 anti-idiotypic antibodies may be administered which do not block the transcription promoter of p53. In another method for treating tumors, gene therapy may be used to replace the amplified dm2 genes with a normal number of dm2 genes to regulate elevated levels of p53. In a further method of treating tumors, anti-sense gene therapy is used to replace the amplified dm2 gene with an antisense dm2 gene.

Methods for determining relative binding affinities may be conducted by methods known in the art. For example, a method for determining whether a p53 protein binds to hsc70 is described by Finlay et al. . in Mol. and Cell. Biol. 8, 531–539 (1988) and by Hinds et al. . in Mol. and Cell. Biol., 7, 2863–2869 (1987). The method described in these papers involves co-immunoprecipitation experiments with anti-p53 and anti-hsc70 antibodies.

EXAMPLES

EXAMPLES 1

Isolation of cDNA clones.

A λgt11 cDNA library prepared from HeLa cells was screened with the mouse mdm2 cDNA as probe under reduced stringency. The cDNA inserts were isolated from positive phages and subcloned into the Bluescript vector for further characterization. A full length cDNA containing the entire coding region was reconstructed from two overlapping clones and completely sequenced using the method of Sanger (Sanger et al. 1977. DNA sequencing with chain-terminating inhibitors. Proc. Natl. Acad. Sci. USA 14:5463–5467).

Generation of monoclonal antibodies against hdm2.

A cDNA clone obtained from the library screening contained the N-terminal coding region of the hdm2 coding region, truncated at the first methionine initiation codon. This CDNA was recombined with the full length hdm2 cDNA to obtain a coding region without leader sequence and the first methionine. This coding sequence was then inserted into the pQE11 vector (Quiagen) to obtain a complete open reading frame with 6 histidine residues fused to the N-terminus of hdm2. The expression plasmid was then introduced into E. coli, the Histidine-hdm2 fusion protein was purified by $Ni^{-2+}$-NTA-agarose (Quiagen) column chromatography. The major protein species in the purified preparation has a mobility similar to in vitro translated hdm2.

Balb/c mice were immunized with the E. coli produced hdm2 protein. Hybridomas were prepared using standard procedures, and screened by enzyme-linked immunosorbent assay and immunoprecipitation of in vitro translated hdm2 protein. Stable clones were established by three rounds of cloning.

Isolation of human dm2 CDNA.

A λgt11 library constructed from HeLa cells was screened using the mouse mdm2 cDNA under conditions of reduced stringency. A total of 14 positive clones were isolated and the cDNA inserts subcloned into the Bluescript vector for further analysis. Preliminary restriction mapping and partial sequencing showed that they represent partial clones for the human dm2 cDNA (Fakharzadeh, S. S. et al. 1991. Tumorigenic potential associated with enhanced expression of a gene that is amplified in a mouse tumor cell line. EMBO J. 10:1565–1569). A full length coding region was constructed from two overlapping cDNA clones and sequenced. The DNA sequence of this cDNA clone, designated hdm2, is similar to the published hdm2 sequence (Oliner, J. D. et al. 1992. Amplification of a gene encoding a p53+ associated protein in human sarcomas. Nature 358:80–83), with complete identitity within the coding region and a few differences in the noncoding regions. The fact that these two cDNA clones were obtained from two very different sources (HeLa cell vs. colon carcinoma), yet have identical coding sequences, suggests that they may represent the wild-type hdm2 coding sequence or a systematic mutation is present in different cancer cells.

EXAMPLE 2

A cohort of 211 soft tissue sarcomas of adults that were clinically and pathologically well characterized were analyzed in this example. In a subgroup of 73 patients, tumor and normal tissue specimens were available. This group of 73 patients was used to address the molecular and biological considerations of the study. However, clinicopathological correlations were conducted using immunohistochemistry and information regarding 211 patients with soft tissue sarcomas obtained from a frequently updated database of clinical and pathological information available for patients at Memorial Sloan-Kettering Cancer Center.

Tissue.

Of the cohort of 211 adult patients affected with soft tissue sarcomas (STS) used for this example, the tumor lesions analyzed included 71 liposarcomas, 53 leiomyosarcomas, 22 malignant fibrous histiocytoma, 15 fibrosarcomas, 15 peripheral nerve sheath tumors (PNST), 13 synovial sarcomas, 4 rhabdomyosarcomas, and 18 undifferentiated sarcomas. The majority of STS analyzed presented as primary tumors (n=129), while the remaining lesions were either recurrent (n=39) or metastatic (n=41). Presentation status in two cases was unknown. Of the 211 STS analyzed, 169 cases were classified as high grade sarcomas, while 39 tumors were considered to be low grade lesions. The grade of 3 cases was unknown. The median and mean follow-up times for this cohort of patients were 29 and 34 months, respectively. Complete follow-up data was available for 209 of the 211 patients.

Tumor specimens were embedded in cryopreservative solution (OCT compound, Miles Laboratories, Elkhart, Ind.), snap frozen in isopentane and stored at −70° C. Representative hematoxylin-eosin stained sections of each block were examined microscopically to confirm the presence of tumor, as well as to evaluate percentage of tumor cells comprising these lesions and extent of tumor necrosis. Adjacent tumor and normal tissue specimens were also collected for molecular genetic assays in 73 of 211 cases (see below). These tissue samples were immediately frozen after surgical removal and stored at −70° C. prior to DNA extraction.

Monoclonal Antibodies and Immunhistochemistry.

A panel of mouse monoclonal antibodies to the p90 gene encoded gene product were used for the present study. Antibody 4B2 detects an epitope located in the amino-terminal region. Antibodies 2A9 and 2A10 identify two distinct epitopes in the central portion of p90. Antibody 4B11 recognizes a sequence located in the carboxy-terminal region of p90. Three mouse monoclonal antibodies detecting different epitopes on p53 proteins were used for the present study. Anti-p53 antibody PAb1801 (Ab-2, Oncogene Science, Manhasset, N.Y.) recognizes an epitope located between amino acids (aa) 32 to 79 of both wild-type and mutant human p53 proteins (Banks, L. et al. (1986) Eur J Biochem 159, 529–534). Antibody PAb240 (Ab-3, Oncogene Science) recognizes a conformational epitope located between aa 156 to 335 characteristic of certain mutant p53 products (Gannon, J. V. et al. (1990) EMBO J 9, 1595–1602). Antibody PAb1620 (Ab-5, Oncogene Science) reacts specifically with wild type p53 (Ball, R. K. et al. (1984) EMBO J 3, 1485–1491). MIgS-Kp I, a mouse monoclonal antibody of the same subclass as the anti-p90 and anti-p53 antibodies, was used as a negative control at similar working dilutions.

The avidin-biotin peroxidase method was performed on 5 um thick frozen tissue sections fixed with cold methanol-acetone (1:1 dilution). Briefly, sections were incubated for 15 minutes with 10% normal horse serum (Organon Tecknika Corp., Westchester, Pa.), followed by a two hour incubation with appropriately diluted primary antibodies (2A9, 4B2 and 4B11 were used at 1:100 dilution, while 2A10 was used at 1:1000 dilution) (Ab-2 was used at 200 ng/ml; Ab-3 at 250 ng/ml and Ab-5 at 3 ug/ml) . After extensive washing, sections were subsequently incubated for 30 minutes with biotinylated horse anti-mouse IgG antibodies at 1:200 dilution (Vector Laboratories, Burlingame, Calif.) and avidin-biotin peroxidase complexes (Vector Laboratories at 1:25 dilution for 30 minutes). Diaminobenzidine (0.06% DAB) was used as the final chromogen and hematoxylin as the nuclear counterstain.

Immunohistochemical evaluation was done by at least two independent investigators, scoring the estimated percentage of tumor cells that showed nuclear staining. Both p90 and p53 nuclear immunoreactivities were classified into three categories defined as follows: negative (<20% tumor cells displaying nuclear staining), heterogeneous (20–79% tumors cells with nuclear reactivities), and homogeneous (≥80% tumor cells with intense nuclear staining).

Southern Blotting and RFLP Analyses.

A human dm2 cDNA fragment probe of 1.6 kb, pHDM (EcoRI), was used in Southern blots to assess gene amplification. A b-actin probe, (EcoRI), was used as a control. Two probes were used for the analysis of allelic deletions of the short arm of chromosome 17, PYNZ22 (17p13.3, D17S5, TaqI) and php53B (17p13.1, p53, BglII). Southern analysis was performed as described (Presti, J. C. et al. (1991) *Cancer Res* 51, 5405; Dalbagni, G. et al. (1993) *Diagnostic Molecular Pathology* 2, 4–13). Briefly, DNA was extracted by the non-organic method developed by Oncor (Oncor, Gaithersburg, MD) from paired normal and tumor samples, digested with the appropriate restriction enzymes, electrophoresed in 0.7% agarose gel, and blotted onto nylon membranes. The membranes were prehybridized with Hybrisol I (Oncor) at 42° C. for one hour, and hybridized with probes labelled to high specific activity with [P32] dCTP overnight. Membranes were then washed and subjected to autoradiography using intensifying screens at −70° C. Densitometry using an Ultrascan XL Laser Densitometer (Pharmacia LKB Biotechnology, Piscataway, N.J.), as well as a Betascope 630 Blot Analyzer (Betagen, Waltham, Mass.), was performed to confirm the results. A case was considered to have a dm2 amplification when it had at least 5 copies gene/cell. Loss of heterozygosity (LOH) was defined as a greater than 40% decrease in signal intensity of an allele in the tumor samples (Presti, J. C. et al. (1991) *Cancer Res* 51, 5405; Olumi, A. F. et al. (1990) *Cancer Res* 50, 7081–7083).

Single Stranded Conformational Polymorphism (SSCP) Analysis and DNA Sequencing.

These studies were performed according to a slight modification of the method reported by Orita et al (Orita, M. et al. (1989) *Genomics* 5, 874–879). Amplifications were performed using 100 ng of genomic DNA extracted from the samples described above. The primers used were obtained from intronic sequences flanking exons 5 through 9 of the human p53 gene, sequences being previously published (Moll, U. M. et al. (1992) *Proc Natl Acad Sci USA* 89, 7262–7266). DNA was amplified following 30 cycles of PCR (30s at 94° C., 30s at 58° C. for exons 8 and 9 and 63° C. for exons 5, 6 and 7, and finally 60s for all samples at 72° C.) using a Thermal Cycler (Perkin Elmer Cetus). Amplified samples were then denatured and loaded onto a nondenaturing acrylamide gel containing 10% glycerol and run at room temperature for 12 –16 hours at 10–12 watts. Gels were dried at 80° C. under vacuum and exposed to X-ray film at −70° C. for 4–16 hours.

Amplification of genomic DNA for sequencing assays was independent of that used for SSCP analysis, using 35 cycles (60s at 94° C., 60s at 58° C and 63° C. —as above, and 90s at 72° C.) . DNA fragments were isolated from 2% low melting point agarose gels, purified and sequenced by the dideoxy method (Sanger, F. et al. (1977) *Proc Natl Acad Sci USA* 74, 5463–5467). Both strands were sequenced for each DNA analyzed, and genomic DNA from control samples containing wild-type p53 were sequenced in parallel to confirm the mutations.

DM2 Amplification and Over-Production of DM2 Proteins.

Amplification of the dm2 gene was detected in 11 of 73 adult soft tissue sarcomas (STS), ranging from 5- to 35 -fold. Dm2 amplifications were more frequently detected in high grade (7 cases) than in low grade (4 cases) STS. Amplifications were more commonly observed in metastatic (3 of 11 cases, 27%) than in primary sarcomas (4 of 48 cases, 8%).

The pattern of immunostaining of anti-dm2 antibodies was first assessed using 3T3-Balbc and 3T3-DM cells. A strong nuclear staining was seen in DM cells, reported to have an amplified dm2 gene and to overexpress dm2 proteins; while Balb-c cells were unreactive (FIG. 4) and have very low levels of dm2 proteins. Six of the 11 amplified cases showed over 20% tumor cells displaying nuclear immunoreactivities with anti-dm2 antibodies. However, the remaining 5 cases were unreactive. Seventeen of the 62 cases with an apparent non-amplified dm2 gene showed elevated levels of dm2 proteins as detected by the dm2 antibodies using tissue sections (dm2-positive phenotype).

p53 Deletions, Point Mutations, and p53 Nuclear Immunoreactivities.

73 pairs of somatic and tumor DNA were examined with two different probes for the short arm of chromosome 17. Deletions of the short arm of chromosome 17 were found in 27 of 51 (53%) informative cases examined. Loss of heterozygosity (LOH) of chromosome 17p was observed in both low and high grade sarcomas. Chromosome 17p LOH was more frequently found in metastatic (6 of 8 cases, 75%) than in primary (13 of 33 cases, 41%) tumors.

To further characterize the specific intragenic mutations of p53 as they may relate to p53 overexpression in these cells, 73 STS were analyzed using SSCP (exons 5 through 9) and those positive for that assay were followed by DNA sequencing. Confirmation of the presence of a mutation was revealed in 14 cases. Eleven of these 14 STS displayed p53 nuclear immunoreactivities for antibody PAb1801. Point mutations were characterized by sequencing in 7 of these 11 sarcomas, 5 showed AT to GC transitions, while 2 were GC to AT transitions. In 4 cases shifts in mobility were detected by SSCP, but no sequencing was conducted to identify the mutation. Three of the 14 mutant cases showed negative immunostaining results for PAb1801. One mutation was identified in codon 165, producing a stop codon. Another case had a C deletion at codon 278, producing a stop codon at position 344. The other mutation occurred in exon 5 affecting a splice donor site. All informative mutants for chromosome 17p status but one had a concomitant deletion of the short arm. In addition, 13 cases showed a positive nuclear staining signal without evidence of point mutations for the exons under study.

Overall, 56 of the 211 STS analyzed displayed a positive nuclear pattern of immunostaining for PAb1801 (Table 1). There was a significant difference between p53-positive phenotype and tumor grade. Moreover, patients affected with STS that showed p53 nuclear immunoreactivities in over 20% tumor cells had significantly reduced survival rates.

TABLE 1

Soft Tissue Sarcomas
High Expression of p53 and mdm-2

|  | p53 over-expression | p53 normal | totals |
| --- | --- | --- | --- |
| mdm-2 over-expression | 22 | 54 | 76/211 (36%) |
| mdm-2 normal | 34 | 101 | 135/211 |
| Totals | 56/211 (26.5%) | 155/211 |  |

Altered Genotype and Phenotype of DM2 and P53: Clinicopathological Implications.

Only one of the subgroup of 73 cases exhibited an amplified dm2 and a mutant p53 gene, and this was a metastatic fibrosarcoma. However, 22 of a total cohort of 211 cases showed positive nuclear immunoreactivities for both dm2 and p53 proteins in consecutive tissue sections (Table 1). The pattern of staining of these molecules, in cases on which they were co-expressed, was in general heterogeneous. When comparing the combined phenotypes (Group A: dm2−/p53−; Group B: dm2+/p53− and dm2−/p53+; and Group C: dm2+/p53+) versus clinicopathological parameters, a correlation was observed between the positive phenotype and variables for a poor prognosis. The data support the conclusion that Group A correlates with the best prognosis, and Group C correlates with the poorest prognosis (see FIG. 3).

EXAMPLE 3 p90 may be used to prepare antibodies that are capable of immunoprecipitating p90 or co-immunoprecipitating p90 with p53. p90 may be isolated from the precipitate and purified. The anti-p90 antibodies may be polyclonal or monoclonal.

One method for preparing polyclonal antibodies to p90 is as follows:
Procedure for p90 antibody production in rabbits:

The p90 protein fragment is at a concentration of 0.7 mg/ml. Immunizations are given as follows:

| Day | |
|---|---|
| Day 0 | 25 µg in 200 µl PBS plus 200 µl RIBI (adjuvant) |
| Day 7 | 50 µg in 200 µl PBS plus 200 µl RIBI (adjuvant) |
| Day 14 | 50 µg in 200 µl PBS plus 200 µl RIBI (adjuvant) |
| Day 21 | REST |
| Day 28 | 50 µg in 200 µl PBS plus 200 µl RIBI |
| Day 39 | Bleed - assay |
| Day 52 | Boost animal with 50 µg in 200 µl PBS plus 200 µl RIBI |
| Day 59 | Bleed - 7 days after last injection assay |
| Day 62 | Exsanguinate |

Bleeds were assayed by ELISA, coating wells at 200 ng/well overnight at 4° C. Block 2% BSA for 1 hr. at 37° C. Make serum dilutions in 1% BSA and incubate 2 hrs. at 37° C. Secondary antibody dilutions (TAGO Goat anti-rabbit peroxidase—cat.# 6430) in 1% BSA and incubate 37° C. for 1 hr. Sera titered out to 1:25000 (cutoff absorbance 0.400 at 450 nm) for the first assay and >50000 for the final assay. Develop with Kirkegaard & Perry TMB Peroxidase Substrate Solution(s) and read absorbance at 450 nm.

EXAMPLE 4

The hybridomas 1F5, 6C10, 1D6, 4B2, 2E12, 3F3, 3G5, 3F8, 6H7, 2A9, 3G9, 1D11, 2A10, 1G2, 4B11 and 5B10 deposited with the ATCC (see above) produce monoclonal antibodies against p90 protein epitopes (see FIG. 1). The following protocols use these monoclonal antibodies and other anti-p90 antibodies as primary antibodies for detecting the DM2 gene-coded product, the p90 protein, by immunohistochemical methods in tissues, preferably human tissues.

The avidin-biotin immunoperoxidase technique is suitable due to the high sensitivity that it renders. Sections of human normal and tumor tissues are cut using a cryostat and placed on microslides. These sections are then incubated with blocking serum, followed by hydrogen peroxide and avidin-biotin blocking. Primary antibodies, i.e. anti-p90 antibodies, are then used at an appropriate concentration. The appropriate concentration is empirically determined for each antibody by performing titrations. Sections are then incubated with biotinylated secondary horse anti-mouse antibodies, followed by avidin-biotin peroxidase complexes. The final reaction is developed using diaminobenzidine. Sections are then counterstained with hematoxylin and mounted with permount for final analysis.

Using such immunohistochemical methods, typically only elevated levels of the p90 protein, not normal levels, are detectable in the tissues since, for those tissues examined in these cases, the monoclonal antibodies can detect only elevated levels of p90 protein in cells.

IMMUNOHISTOCHEMISTRY

AVIDIN-BIOTIN-PEROXIDASE METHOD PARAFFIN EMBEDDED TISSUE SECTIONS

1) Place 5 µm tissue sections on poly-L-lysine coated slides.

2) Place sections in 60C oven for 30 minutes to melt paraffin.

3) Cool slides at room temperature then process for deparaffinization and rehydration:
  xylene —3 times (5 minutes each)
  100% ethanol —3 times (3 minutes each)
  35 95% ethanol —3 times (3 minutes each)

4) Wash in distilled $H_2O$ and transfer to PBS.

5) Quench with 1% $H_2O_2$ for 15 minutes to eliminate endogenous peroxidase activity.

6) Wash in PBS—3 times.

7) In tissues that contain biotin (such as liver, kidney, brain, etc.), apply Avidin-Biotin blocking kit (Vector) in order to eliminate endogenous biotin activity. Solutions should be applied subsequently (Avidin, then biotin) and slides should be incubated for 15 minutes with each solution.

8) Wash in PBS.

9) Enzyme digestion—enzyme selection determined empirically as optimally for each antibody.
Common enzymes:
  Pepsin (Porcine Stomach Mucosa, Sigma): HCL (250 ml distilled $H_2O$ +200 µl HCl)+0.25 grams pepsin →incubation 30 minutes.
  Trypsin (Bovine Pancreas Type I, Sigma) : 250 ml TRIS+ 0.0625 grams trypsin→incubate for 5 minutes; wash in distilled $H_2O$, then incubate for 15 minutes with trypsin inhibitor (Sigma) :250 ml PBS +0.025 gms trypsin inhibitor.
  Pronase (Calbiochem Behring) : 250 ml TRIS+0.0055 gms pronase→incubate for 4 minutes;
  Ficin (suspension—Sigma)—ready to use, dropwise, incubation 45 minutes.
  Saponin (detergent—Sigma) : 250 ml distilled $H_2O$+ 0.125 gms Saponin→incubation 30 minutes.

10) Wash slides in distilled $H_2O$ and transfer to PBS.

11) Apply blocking serum—10% normal serum (species specific—same species as the secondary antibody) —incubation 20–30 minutes.

12) Vacuum suction off the blocking serum and apply appropriately diluted primary antibody—incubation overnight at 4° C. in a humid chamber. The primary antibody is selected from the anti-p90 monoclonal antibodies produced by the following hybridomas: 1F5, 6C10, 1D6, 4B2, 2E12, 3F3, 3G5, 3F8, 6H7, 2A9, 3G9, 1D11, 2A10, 1G2, 4B11 and 5B10. The appropriate dilution of the primary antibody is an empirically determined optimal concentration.

13) Extensive washing with PBS→3 changes (5 minutes each)

14) Apply appropriately diluted biotinylated secondary antibody→30 minutes incubation.

15) Wash with PBS (3×5 minutes).

16) Avidin-biotin complex (Vector) diluted 1:25 (equal ratio A B)→incubation 30 minutes.

17) Wash with PBS (3×5 minutes).

18) Substrate chromogen solution: peroxidase-diaminobenzidine (0.06% DAB) (5 mg DAB/100 ml PBS +100 ul 0.3% H$_2$O$_2$) Incubate until desired color intensity has developed (approximately 5 minutes)

19) Hematoxylin counterstain.

IMMUNOHISTOCHEMISTRY

AVIDIN-BIOTIN-PEROXIDASE METHOD—FROZEN TISSUE SECTIONS 1. 5 μm frozen tissue sections—leave at room temperature for at least 30 minutes to thaw and dry sections.

2. Apply proper fixative for 10 minutes (fixative optimally chosen for each antibody).

3. Quench with 0.1% H$_2$O$_2$ for 15 minutes to eliminate endogenous peroxidase activity.

4. Wash in PBS—3x.

5. Avidin-biotin blocking kit in tissues rich with endogenous biotin. Avidin—incubate 15 minutes, wash with PBS and then biotin –15 minutes.

6. Wash in PBS—3x.

7. Apply blocking serum—10% normal serum (species specific, same species as the secondary antibody) 10–30 minutes incubation in humid chamber.

8. Suction off the blocking serum and apply appropriately diluted primary antibody incubation 1–2 hours. The primary antibody is selected from the anti-p90 monoclonal antibodies produced by the following hybridomas: 1F5, 6C10, 1D6, 4B2, 2E12, 3F3, 3G5, 3F8, 6H7, 2A9, 3G9, 1D11, 2A10, 1G2, 4B11 and 5B10. The appropriate dilution of the primary antibody is an empirically determined optimal concentration, typically 1–1000 volume/volume of hybridoma supernatant/phosphate buffered saline (PBS).

9. Wash extensively in PBS.

10. Apply appropriately diluted biotinylated secondary antibody –30 minutes incubation.

11. Wash with PBS—3x.

12. Avidin-biotin complex (Vector) dilution 1:25 (equal ratio A:B)—30 minutes.

13. Wash PBS and PBS/Triton—3x.

14. Substrate chromagen solution: peroxidase-diaminobenzidine (0.06% DAB) approximately 5 minutes.

15. Hematoxylin counterstain.

We claim:

1. A method of assessing a subject's cancer prognosis, the method comprising:
(a) obtaining a biological sample from the subject,
(b) determining whether the level of either p53 or dm2 in the sample is abnormally elevated; and
(c) classifying a biological sample into one of three groups, the first group comprises no abnormal elevation of either the level of p53 or dm2, the second group comprises abnormal elevation of the level of p53 and no abnormal elevation of the level of dm2 or abnormal elevation of the level of dm2 and no abnormal elevation of the level of p53, and the third group comprises abnormal elevation of the level of both p53 and dm2, whereby the first group indicates the best prognosis, the second group indicates an intermediate prognosis, and the third group indicates the worst prognosis.

2. A method according to claim 1, wherein the level of dm2 gene amplification or expression is determined by using probes.

3. A method according to claim 2, wherein the probes are antibodies.

4. A method according to claim 3, wherein th antibodies are monoclonal.

5. A method of detecting in a biological sample cancer cells or cells at risk of becoming cancerous or pre-cancerous, wherein th cells contain at least one normal p53 allele, the method comprising determining whether the level of dm2 in the biological sample is abnormally elevated in comparison with the level of dm2 expression in normal biological samples, whereby an abnormally elevated level of dm2in the assayed biological sample indicates cancer cells or cells at risk of becoming cancerous or pre-cancerous.

6. A method according to claim 5, wherein the elevated level is determined by immunohistochemical staining of the biological sample.

7. A method according to claim 5, wherein the level of dm2 gene amplification or expression is determined by using probes.

8. A method according to claim 7, wherein the probes are nucleic acid probes.

9. A method according to claim 7, wherein the probes are antibodies.

10. A method according to claim 9, wherein the antibodies are monoclonal.

11. A method according to claim 4 or 10, wherein the monoclonal antibody is produced by hybridoma 3G5, deposited under ATCC Accession No. HB 11182.

12. A method according to claim 4 or 10, wherein the monoclonal antibody is produced by hybridoma 4B11, deposited under ATCC Accession No. HB 11183.

13. A method according to claim 4 or 10, wherein the monoclonal antibody is produced by hybridoma 2A10, deposited under ATCC Accession No. HB 11184.

14. A method according to claim 4 or 10, wherein the monoclonal antibody is produced by hybridoma 2A9, deposited under ATCC Accession No. HB 11185.

15. A method according to claim 4 or 10, wherein the monoclonal antibody is produced by hybridoma 4B2, deposited under ATCC Accession No. HB 11186.

16. A method according to claim 4 or 10, wherein the monoclonal antibody recognizes the same epitope or epitopes as those recognized by a monoclonal antibody produced by a hybridoma selected from the group consisting of hybridoma 3G5, deposited under ATCC Accession No. HB 11182; hybridoma 4B11, deposited under ATCC Accession No. HB 11183; hybridoma 2A10, deposited under ATCC Accession No. HB 11184; hybridoma 2A9, deposited under ATCC Accession No. HB 11185; and hybridoma 4B2, deposited under ATCC Accession No. HB 11186.

17. A method according to claim 4 or 10, wherein the monoclonal antibody competes with a monoclonal antibody produced by a hybridoma selected from the group consisting of hybridoma 3G5, deposited under ATCC Accession No. HB 11182, hybridoma 4B11, deposited under ATCC Accession No. HB 11183; hybridoma 2A1 0, deposited under ATCC Accession No HB 11184; hybridoma 2A9, deposited under ATCC Accession N HB 11185, and hybridoma 4B2, deposited under ATCC Accession No. HB11186 for binding to the same epitope or epitopes as those recognized by a monoclonal antibody produced by any of these hybridomas.

18. A method according to claim 17, wherein the competing monoclonal antibody blocks between 50–100% of the epitope or epitopes recognized by the monoclonal antibody produced by a hybridoma selected from the group consisting of hybridoma 3G5, deposited under ATCC Accession No. HB 11182; hybridoma 4B11, deposited under ATCC Accession No. HB 11183; hybridoma 2A10, deposited under ATCC Accession No. HB 11184; hybridoma 2A9, deposited under ATCC Accession No. HB 11185; and hybridoma 4B2, deposited under ATCC Accession No. HB 11186.

19. A method of diagnosing cancer by determining the level of p53 and dm2 in a biological sample, whereby an elevated level of either p53 or dm2 or both p53 and dm2 indicates a cancer diagnosis.

20. A method of predicting the progress of cancer by determining the level of p53 and dm2 in a biological sample, whereby an elevated level of either p53 or dm2 or both p53 and dm2 indicates a poor prognosis.

21. The monoclonal antibody produced by hybridoma 3G5, deposited under ATCC Accession No. HB 11182.

22. The monoclonal antibody produced by hybridoma 4B11, deposited under ATCC Accession No. HB 11183.

23. The monoclonal antibody produced by hybridoma 2A10, deposited under ATCC Accession No. HB 11184.

24. The monoclonal antibody produced by hybridoma 2A9, deposited under ATCC Accession No. HB 11185.

25. The monoclonal antibody produced by hybridoma 4B2, deposited under ATCC Accession No. HB 11186.

26. A monoclonal antibody of claim 21, 22, 23, 24 or 25 labeled with a detectable marker.

27. A method for imaging tumors which comprises contacting the tumor to be imaged with an anti-dm2 antibody of claim 26, under conditions such that the antibody binds to the tumor and detecting the antibody bound thereto, thereby imaging the tumor.

28. A monoclonal antibody that recognizes the same epitope or epitopes as those recognized by a monoclonal antibody produced by a hybridoma selected from the group consisting of hybridoma 3G5, deposited under ATCC Accession No. HB 11182; hybridoma 4B11, deposited under ATCC Accession No. HB 11183; hybridoma 2A10, deposited under ATCC Accession No. HB 11184; hybridoma 2A9, deposited under ATCC Accession No. HB 11185; and hybridoma 4B2, deposited under ATCC Accession No. HB 11186.

29. A monoclonal antibody that competes with a monoclonal antibody produced by a hybridoma selected from the group consisting of hybridoma 3G5, deposited under ATCC Accession No. HB 11182; hybridoma 4B11, deposited under ATCC Accession No. HB 11183; hybridoma 2A10, deposited under ATCC Accession No. HB 11184; hybridoma 2A9, deposited under ATCC Accession N. HB 11185; and hybridoma 4B2, deposited under ATCC Accession No. HB11186 for binding to the same epitope or epitopes as those recognized by a monoclonal antibody produced by any of these hybridomas.

30. A monoclonal antibody according to claim 73 that blocks between 50–100% of the epitope or epitopes recognized by the monoclonal antibody produced by a hybridoma selected from the group consisting of hybridoma 3G5, deposited under ATCC Accession No. HB 11182; hybridoma 4B11, deposited under ATCC Accession No. HB 11183; hybridoma 2A10, deposited under ATCC Accession No. HB 11184; hybridoma 2A9, deposited under ATCC Accession No. HB 11185; and hybridoma 4B2, deposited under ATCC Accession No. HB 11186.

31. A hybridoma selected from the group consisting of hybridoma 3G5, deposited under ATCC Accession No. HB 11182; hybridoma 4B11, deposited under ATCC Accession No. HB 11183; hybridoma 2A10, deposited under ATCC Accession No. HB 11184; hybridoma 2A9, deposited under ATCC Accession No. HB 11185; and hybridoma 4B2, deposited under ATCC Accession No. HB 11186.

32. A diagnostic kit comprising:
  (a) a container comprising an anti-p53 antibody that recognizes a p53 protein; and
  (b) a container comprising an anti-dm2 antibody that recognizes a dm2 protein.

33. A diagnostic kit of claim 32, wherein the antibodies are labeled.

34. A diagnostic kit of claim 32, further comprising:
  (a) a labeled antibody that recognizes the anti-p53 antibody; and
  (b) a labeled antibody that recognizes the anti-dm2 antibody.

* * * * *

UNITED STATES PATENT AND TRADEMARK OFFICE
CERTIFICATE OF CORRECTION

PATENT NO. : 5,843,684

DATED : December 1, 1998

INVENTOR(S) : Arnold J. Levine, et al

It is certified that error appears in the above-identified patent and that said Letters Patent is hereby corrected as shown below:

Column 1, line 14, please insert --- The U.S. government has a paid-up license in this invention and the right in limited circumstances to require the patent owner to license others on reasonable terms as provided for by the terms of grant no. 5 P01 CA 41086 awarded by the National Institute of Health. ---

Signed and Sealed this

Sixteenth Day of November, 1999

*Attest:*

Q. TODD DICKINSON

*Attesting Officer*     *Acting Commissioner of Patents and Trademarks*